United States Patent
Olah et al.

(10) Patent No.: US 7,704,369 B2
(45) Date of Patent: Apr. 27, 2010

(54) ELECTROLYSIS OF CARBON DIOXIDE IN AQUEOUS MEDIA TO CARBON MONOXIDE AND HYDROGEN FOR PRODUCTION OF METHANOL

(75) Inventors: George A. Olah, Beverly Hills, CA (US); G. K. Surya Prakash, Hacienda Heights, CA (US)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 12/171,904

(22) Filed: Jul. 11, 2008

(65) Prior Publication Data

US 2009/0014336 A1 Jan. 15, 2009

Related U.S. Application Data

(60) Provisional application No. 60/949,723, filed on Jul. 13, 2007.

(51) Int. Cl.
C25B 3/00 (2006.01)
C07C 27/00 (2006.01)

(52) U.S. Cl. .................. 205/450; 568/700
(58) Field of Classification Search ............ 205/450, 205/555, 628, 638; 568/700
See application file for complete search history.

(56) References Cited

U.S. PATENT DOCUMENTS 4,022,672 A * 5/1977 Alvarez et al. ............... 205/461
6,797,830 B2 * 9/2004 Tanaka et al. ................ 549/273

2006/0048517 A1 * 3/2006 Fradette et al. ................ 60/772
2007/0045125 A1   3/2007 Hartvigsen et al. .......... 205/637
2007/0129450 A1 * 6/2007 Barnicki et al. ............. 518/704

FOREIGN PATENT DOCUMENTS

JP         08246177 A  *  9/1996
RU         2 062 750 C1     6/1996
WO         WO 02083272 A1 * 10/2002

OTHER PUBLICATIONS

Kobayashi et al., "Novel CO2 Electrochemical Reduction to Methanol for H2 Storage", Energy & Fuels (no month, 2004), vol. 18, pp. 285-286.*
Sanchez et al., "Electrochemical Approaches to Alleviation of the Problem of Carbon Dioxide Accumulation", Pure Appl. Chem. (no month, 2001), vol. 73, No. 12, pp. 1917-1927.*
Ogden et al., "Electrolytic Hydrogen From Thin-Film Solar Cells", Int. J. Hydrogen Energy (no month, 1990), vol. 15, No. 3, pp. 155-169.*

(Continued)

Primary Examiner—Edna Wong
(74) Attorney, Agent, or Firm—Winston & Strawn LLP

(57) ABSTRACT

An environmentally beneficial method of producing methanol from varied sources of carbon dioxide including flue gases of fossil fuel burning power plants, industrial exhaust gases or the atmosphere itself. Converting carbon dioxide by an electrochemical reduction of carbon dioxide in a divided electrochemical cell that includes an anode in one cell compartment and a metal cathode electrode in another cell compartment that also contains an aqueous solution comprising methanol and an electrolyte of one or more alkyl ammonium halides, alkali carbonates or combinations thereof to produce therein a reaction mixture containing carbon monoxide and hydrogen which can be subsequently used to produce methanol while also producing oxygen in the cell at the anode.

17 Claims, 2 Drawing Sheets

OTHER PUBLICATIONS

Naitoh et al., "Electrochemical Reduction of Carbon Dioxde in Methanol at Low Temperature", Electrochimica Acta (no month, 1993), vol. 38, No. 15, pp. 2177-2179.*

Saeki et al., "Electrochemical Reduction of CO2 with High Current Density in a CO2+Methanol Medium II. CO Formation Promoted by Tetrabutylammonium Cation", J. of Electroanal. Chem. (no month, 1995), vol. 390, pp. 77-82.*

Sanchez-Sanchez et al., "Electrochemical Approaches to Alleviation of the Problem of Carbon Dioxide Accumulation", Pure Appl. Chem. (no month, 2001), vol. 73, No. 12, pp. 1917-1927.*

Ogura et al., "Catalytic Conversion of CO and CO2 into Methanol with a Solar Cell", J. of Molecular Catalysis (no month, 1986), vol. 34, pp. 309-311.*

Azuma et al., "Electrochemical Reduction of Carbon Dioxde on Various Metal Electrodes in Low-Temperature Aqueous $KHCO_3$ Media," J. Electrochem. Soc., 137(6): 1772-1778 (1990).

Hori et al., "Electrocatalytic Process of CO Selectivity in Electrochemical Reduction of CO2 at Metal Electrodes in Aqueous Media," Electrochimica Acta, 39(11/12): 1833-1839 (1994).

Naitoh et al., "Electrochemical Reduction of Carbon Dioxde in Methanol at Low Temperature," Electrochimica Acta, 38(15): 2177-2179 (1993).

International Search Report and the Written Opinion of the International Searching Authority, application No. PCT/US2008/069803, dated Feb. 6, 2009.

Saeki et al. (Electrochemical Reduction of CQ with High Current Density In a $CO_2$-Methanol Medium, *J. Phys. Chem.* 1995, 99, 8440-8446).

Donald A. Tryk et al., "Electrochemists Enlisted in War, The Carbon Dioxide Reduction Battle", The Electrochemical Society*Interface*, pp. 32-36 (2001).

* cited by examiner

FIG. 1: Methanol derived chemical products and materials

PRIOR ART

ELECTROLYSIS OF CARBON DIOXIDE IN AQUEOUS MEDIA TO CARBON MONOXIDE AND HYDROGEN FOR PRODUCTION OF METHANOL

This application claims the benefit of provisional application No. 60/949,723 filed Jul. 13, 2007, the entire content of which is expressly incorporated herein by reference thereto.

BACKGROUND

Hydrocarbons are essential in modern life. Hydrocarbons are used as fuel and raw material in various fields, including the chemical, petrochemical, plastics, and rubber industries. Fossil fuels, such as coal, oil and gas, are composed of hydrocarbons with varying ratios of carbon and hydrogen, and is non-renewably used when combusted, forming carbon dioxide and water. Despite their wide application and high demand, fossil fuels present a number of disadvantages, including the finite reserve, irreversible combustion and contribution to air pollution and global warming. Considering these disadvantages, and the increasing demand for energy, alternative sources of energy are needed.

One such alternative frequently mentioned is hydrogen, and the so-called "hydrogen economy." Hydrogen is beneficial as a clean fuel, producing only water when combusted. Free hydrogen, however, is not a natural energy source, and its generation from hydrocarbons or water is a highly energy-consuming process. Further, when hydrogen is produced from hydrocarbons, any claimed benefit of hydrogen as a clean fuel is outweighed by the fact that generation of hydrogen itself, mainly by reforming of natural gas, oil or coal to synthesis gas ("syn-gas") a mixture of CO and $H_2$, is far from clean. It consumes fossil fuels, with a quarter of the energy of the fuel being lost as heat. Hydrogen is also not a convenient energy storage medium because it is difficult and costly to handle, store, transport and distribute. As it is extremely volatile and potentially explosive, hydrogen gas requires high-pressure equipment, costly and non-existent infrastructure, special materials to minimize diffusion and leakage, and extensive safety precautions to prevent explosions.

It was suggested that a more practical alternative is methanol. Methanol, $CH_3OH$, is the simplest liquid oxygenated hydrocarbon, differing from methane ($CH_4$) by a single additional oxygen atom. Methanol, also called methyl alcohol or wood alcohol, is a colorless, water-soluble liquid with a mild alcoholic odor, and is easy to store and transport. It freezes at −97.6° C., boils at 64.6° C., and has a density of 0.791 at 20° C.

Methanol is not only a convenient and safe way to store energy. Methanol either can be blended with gasoline or diesel and used as fuels, for example in internal combustion engines or electricity generators. One of the most efficient use of methanol is in fuel cells, particularly in direct methanol fuel cell (DMFC), in which methanol is directly oxidized with air to carbon dioxide and water while producing electricity.

Contrary to gasoline, which is a complex mixture of many different hydrocarbons and additives, methanol is a single chemical compound. It contains about half the energy density of gasoline, meaning that two liters of methanol provides the same energy as a liter of gasoline. Even though methanol's energy content is lower, it has a higher octane rating of 100 (average of the research octane number (RON) of 107 and motor octane number (MON) of 92), which means that the fuel/air mixture can be compressed to a smaller volume before being ignited. This allows the engine to run at a higher compression ratio (10-11 to 1 against 8-9 to 1 of a gasoline engine), more efficiently than a gasoline-powered engine. Efficiency is also increased by methanol's higher "flame speed," which enables faster, more complete fuel combustion in the engines. These factors explain the high efficiency of methanol despite its lower energy density than gasoline. Further, to render methanol more ignitable even under the most frigid conditions, methanol can be mixed with gasoline, with volatile compounds (e.g., dimethyl ether), with other components or with a device to vaporize or atomize methanol. For example, an automotive fuel can be prepared by adding methanol to gasoline with the fuel having a minimum gasoline content of at least 15% by volume (M85 fuel) so that it can readily start even in low temperature environments. Of course, any replacement of gasoline in such fuels will conserve oil resources, and the amount of methanol to add can be determined depending upon the specific engine design.

Methanol has a latent heat of vaporization of about 3.7 times higher than gasoline, and can absorb a significantly larger amount of heat when passing from liquid to gas state. This helps remove heat away from the engine and enables the use of an air-cooled radiator instead of a heavier water-cooled system. Thus, compared to a gasoline-powered car, a methanol-powered engine provides a smaller, lighter engine block, reduced cooling requirements, and better acceleration and mileage capabilities. Methanol is also more environment-friendly than gasoline, and produces low overall emissions of air pollutants such as hydrocarbons, $NO_x$, $SO_2$ and particulates.

Methanol is also one of the safest fuels available. Compared to gasoline, methanol's physical and chemical properties significantly reduce the risk of fire. Methanol has lower volatility, and methanol vapor must be four times more concentrated than gasoline for ignition to occur. Even when ignited, methanol burns about four times slower than gasoline, releases heat only at one-eighth the rate of gasoline fire, and is far less likely to spread to surrounding ignitable materials because of the low radiant heat output. It has been estimated by the EPA that switching from gasoline to methanol would reduce incidence of fuel-related fire by 90%. Methanol burns with a colorless flame, but additives can solve this problem.

Methanol also provides an attractive and more environment-friendly alternative to diesel fuel. Methanol does not produce smoke, soot, or particulates when combusted, in contrast to diesel fuel, which generally produces polluting particles during combustion. Methanol also produces very low emissions of NOx because it burns at a lower temperature than diesel. Furthermore, methanol has a significantly higher vapor pressure compared to diesel fuel, and the higher volatility allows easy start even in cold weather, without producing white smoke typical of cold start with a conventional diesel engine. If desired, additives or ignition improvers, such as octyl nitrate, tetrahydrofurfuryl nitrate, peroxides or higher alkyl ethers, can be added to bring methanol's cetane rating to the level closer to diesel. Methanol can also be used in the manufacture of biodiesel fuels by esterification of fatty acids.

Closely related and derived from methanol, and also a desirable alternative fuel is dimethyl ether. Dimethyl ether is easily obtained by methanol dehydration. Dimethyl ether (DME, $CH_3OCH_3$), the simplest of all ethers, is a colorless, nontoxic, non-corrosive, non-carcinogenic and environmentally friendly chemical that is mainly used today as an aerosol propellant in spray cans, in place of the banned CFC gases. DME has a boiling point of −25° C., and is a gas under ambient conditions. DME has no propensity to form peroxides unlike higher homologous ethers. DME is, however, easily handled as liquid and stored in pressurized tanks, much like liquefied petroleum gas (LPG). The interest in dimethyl ether as alternative fuel lies in its high cetane rating of 55 to 60, which is much higher than that of methanol and is also higher than the cetane rating of 40 to 55 of conventional diesel fuels. The cetane rating indicates that DME can be effectively used in diesel engines. Advantageously, DME, like methanol, is clean burning, and produces no soot particulates, black smoke or $SO_2$, and only very low amounts of $NO_x$ and other emissions even without after-treatment of its exhaust gas. Some of the physical and chemical properties of DME, in comparison to diesel fuel, are shown in Table 1.

TABLE 1

Comparison of the physical properties of DME and diesel fuel

|  | DME | Diesel fuel |
| --- | --- | --- |
| Boiling point ° C. | −24.9 | 180-360 |
| Vapor pressure at 20° C. (bar) | 5.1 | — |
| Liquid density at 20° C. (kg/m³) | 668 | 840-890 |
| Heating value (kcal/kg) | 6,880 | 10,150 |
| Cetane number | 55-60 | 40-55 |
| Autoignition temperature (° C.) | 235 | 200-300 |
| Flammability limits in air (vol %) | 3.4-17 | 0.6-6.5 |

Currently, DME is exclusively produced by dehydration of methanol. A method for synthesizing DME directly from synthesis gas by combining the methanol synthesis and dehydration steps in a single process has also been developed.

Another methanol derivative is dimethyl carbonate (DMC), which can be obtained by converting methanol with phosgene or by oxidative carbonylation of the methanol. DMC has a high cetane rating, and can be blended into diesel fuel in a concentration up to 10%, reducing fuel viscosity and improving emissions.

Methanol and its derivatives, e.g., DME, DMC, and biodiesel, have many existing and potential uses. They can be used, for example, as a substitute for gasoline and diesel fuel in ICE-powered cars with only minor modifications to the existing engines and fuel systems. Methanol can also be used in fuel cells, for fuel cell vehicles (FCVs), which are considered to be the best alternative to ICEs in the transportation field. DME is also a potential substitute for LNG and LPG for heating homes and in industrial uses.

Methanol is also useful in reforming to hydrogen. In an effort to address the problems associated with hydrogen storage and distribution, suggestions have been made to use liquids rich in hydrogen such as gasoline or methanol as a source of hydrogen in vehicles via an on-board reformer. It is also considered that methanol is the safest of all materials available for such hydrogen production. Further, because of the high hydrogen content of liquid methanol, even compared to pure cryogenic hydrogen (98.8 g of hydrogen in a liter of methanol at room temperature compared to 70.8 g in liquid hydrogen at −253° C.), methanol is an excellent carrier of hydrogen fuel. The absence of C—C bonds in methanol, which are difficult to break, facilitates its transformation to pure hydrogen with 80 to 90% efficiency.

In contrast to a pure hydrogen-based storage system, a reformer system is compact, containing on a volume basis more hydrogen than even liquid hydrogen, and is easy to store and handle without pressurization. A methanol steam reformer is also advantageous in allowing operation at a much lower temperature (250-350° C.) and for being better adapted to on-board applications. Furthermore, methanol contains no sulfur, a contaminant for fuel cells, and no nitrogen oxides are formed from a methanol reformer because of the low operating temperature. Particulate matter and $NO_x$ emissions are virtually eliminated, and other emissions are minimal. Moreover, methanol allows refueling to be as quick and easy as with gasoline or diesel fuel. Thus, an on-board methanol reformer enables rapid and efficient delivery of hydrogen from liquid fuel that can be easily distributed and stored in the vehicle. To date, methanol is the only liquid fuel that has been processed and demonstrated on a practical scale as suitable for fuel use in a fuel cell for transportation applications.

In addition to on-board reforming, methanol also enables convenient production of hydrogen in fueling stations for refueling hydrogen fuel cell vehicles. A fuel cell, an electrochemical device that converts free chemical energy of fuel directly into electrical energy, provides a highly efficient way of producing electricity via catalytic electrochemical oxidation. For example, hydrogen and oxygen (air) are combined in an electrochemical cell-like device to produce water and electricity. The process is clean, with water being the only byproduct. However, because hydrogen itself must first be produced in an energy-consuming process, by electrolysis or from a hydrocarbon source (fossil fuel) with a reformer, hydrogen fuel cells are still necessarily limited in utility.

A system for producing high purity hydrogen has been developed by steam reforming of methanol with a highly active catalyst, which allows operation at a relatively low temperature (240-290° C.) and enables flexibility in operation as well as rapid start-up and stop. These methanol-to-hydrogen (MTH) units, ranging in production capacity from 50 to 4000 m³ $H_2$ per hour, are already used in various industries, including the electronic, glass, ceramic, and food processing industries, and provide excellent reliability, prolonged life span, and minimal maintenance. Operating at a relatively low temperature, the MTH process has a clear advantage over reforming of natural gas and other hydrocarbons which must be conducted at above 600° C., because less energy is needed to heat methanol to the appropriate reaction temperature.

The usefulness of methanol has led to development of other reforming processes, for example, a process known as oxidative steam reforming, which combines steam reforming, partial oxidation of methanol, and novel catalyst systems. Oxidative steam reforming produces high purity hydrogen with zero or trace amounts of CO, at high methanol conversion and temperatures as low as 230° C. It has the advantage of being, contrary to steam reforming, an exothermic reaction, therefore minimizing energy consumption. There is also autothermal reforming of methanol, which combines steam reforming and partial oxidation of methanol in a specific ratio and addresses any drawback of an exothermic reaction by producing only enough energy to sustain itself. Autothermal reforming is neither exothermic nor endothermic, and does not require any external heating once the reaction temperature is reached. Despite the aforementioned possibilities, hydrogen fuel cells must use highly volatile and flammable hydrogen or reformer systems.

U.S. Pat. No. 5,599,638 discloses a simple direct methanol fuel cell (DMFC) to address the disadvantages of hydrogen fuel cells. In contrast to a hydrogen fuel cell, the DMFC is not dependent on generation of hydrogen by processes such as electrolysis of water or reformation of natural gas or hydrocarbon. The DMFC is also more cost effective because methanol, as a liquid fuel, does not require cooling at ambient temperatures or costly high pressure infrastructure and can be used with existing storage and dispensing units, unlike hydrogen fuel, whose storage and distribution requires new infrastructure. Further, methanol has a relatively high theoretical volumetric energy density compared to other systems such as conventional batteries and the $H_2$-PEM fuel cell. This is of great importance for small portable applications (cellular phones, laptop computers, etc.), for which small size and weight of energy unit is desired.

The DMFC offers numerous benefits in various areas, including the transportation sector. By eliminating the need for a methanol steam reformer, the DMFC significantly reduces the cost, complexity and weight of the vehicle, and improves fuel economy. A DMFC system is also comparable in its simplicity to a direct hydrogen fuel cell, without the cumbersome problems of on-board hydrogen storage or hydrogen producing reformers. Because only water and $CO_2$ are emitted, emissions of other pollutants (e.g., $NO_x$, PM, $SO_2$, etc.) are eliminated. Direct methanol fuel cell vehicles are expected to be virtually zero emission vehicles (ZEV), and use of methanol fuel cell vehicles offers to nearly eliminate air pollutants from vehicles in the long term. Further, unlike ICE vehicles, the emission profile is expected to remain nearly unchanged over time. New membranes based on hydrocarbon or hydrofluorocarbon materials with reduced cost and crossover characteristics have been developed that allow room temperature efficiency of 34%.

Methanol as indicated provides a number of important advantages as transportation fuel. Contrary to hydrogen, methanol does not require any energy intensive procedures for pressurization or liquefaction. Because it is a liquid at room temperature, it can be easily handled, stored, distributed and carried in vehicles. It can act as an ideal hydrogen carrier for fuel cell vehicles through on-board methanol reformers, and can be used directly in DMFC vehicles.

Methanol is also an attractive source of fuel for static applications. For example, methanol can be used directly as fuel in gas turbines to generate electric power. Gas turbines typically use natural gas or light petroleum distillate fractions as fuel. Compared to such fuels, methanol can achieve higher power output and lower $NO_x$ emissions because of its lower flame temperature. Since methanol does not contain sulfur, $SO_2$ emissions are also eliminated. Operation on methanol offers the same flexibility as on natural gas and distillate fuels, and can be performed with existing turbines, originally designed for natural gas or other fossil fuels, after relatively easy modification. Methanol is also an attractive fuel since fuel-grade methanol, with lower production cost than higher purity chemical-grade methanol, can be used in turbines. Because the size and weight of a fuel cell is of less importance in static applications than mobile applications, various fuel cells other than PEM fuel cells and DMFC, such as phosphoric acid, molten carbonate and solid oxide fuel cells (PAFC, MCFC, and SOFC, respectively), can also be used.

In addition to use as fuels, methanol and methanol-derived chemicals have other significant applications in the chemical industry. Today, methanol is one of the most important feedstock in the chemical industry. Most of the 32 million tons of annually produced methanol is used to manufacture a large variety of chemical products and materials, including basic chemicals such as formaldehyde, acetic acid, MTBE (although it is increasingly phased out in the U.S. for environmental reasons), as well as various polymers, paints, adhesives, construction materials, and others. Worldwide, almost 70% of methanol is used to produce formaldehyde (38%), methyl-tert-butyl ether (MTBE, 20%) and acetic acid (11%). Methanol is also a feedstock for chloromethanes, methylamines, methyl methacrylate, and dimethyl terephthalate, among others. These chemical intermediates are then processed to manufacture products such as paints, resins, silicones, adhesives, antifreeze, and plastics. Formaldehyde, produced in large quantities from methanol, is mainly used to prepare phenol-, urea- and melamine-formaldehyde and polyacetal resins as well as butanediol and methylene bis(4-phenyl isocyanate) (MDI; MDI foam is used as insulation in refrigerators, doors, and in car dashboards and bumpers). Formaldehyde resins are predominantly employed as an adhesive in a wide variety of applications, e.g., manufacture of particle boards, plywood and other wood panels. Examples of methanol-derived chemical products and materials are shown in FIG. 1.

In producing basic chemicals, raw material feedstock constitutes typically up to 60-70% of the manufacturing costs. The cost of feedstock therefore plays a significant economic role. Because of its lower cost, methanol is considered a potential feedstock for processes currently utilizing more expensive feedstocks such as ethylene and propylene, to produce chemicals including acetic acid, acetaldehyde, ethanol, ethylene glycol, styrene, and ethylbenzene, and various synthetic hydrocarbon products. For example, direct conversion of methanol to ethanol can be achieved using a rhodium-based catalyst, which has been found to promote the reductive carbonylation of methanol to acetaldehyde with selectivity close to 90%, and a ruthenium catalyst, which further reduces acetaldehyde to ethanol. The possibility of producing ethylene glycol via methanol oxidative coupling instead of the usual process using ethylene as feedstock is also pursued, and significant advances for synthesizing ethylene glycol from dimethyl ether, obtained by methanol dehydration, have also been made.

Conversion of methanol to olefins such as ethylene and propylene, also known as methanol to olefin (MTO) technology, is particularly promising considering the high demand for olefin materials, especially in polyolefin production. The MTO technology is presently a two-step process, in which natural gas is converted to methanol via syn-gas and methanol is then transformed to olefin. It is considered that methanol is first dehydrated to dimethyl ether (DME), which then reacts to form ethylene and/or propylene. Small amounts of butenes, higher olefins, alkanes, and aromatics are also formed.

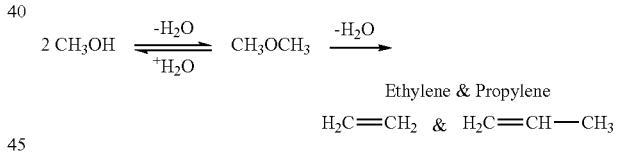

Ethylene & Propylene $H_2C{=}CH_2$ & $H_2C{=}CH{-}CH_3$

Various catalysts, e.g., synthetic aluminosilicate catalysts, such as ZSM-5 (a zeolite developed by Mobil), silicoaluminophosphate (SAPO) molecular sieves such as SAPO-34 and SAPO-17 (UOP), as well as bi-functional supported acid-base catalysts such as tungsten oxide over alumina ($WO_3/Al_2O_3$), have been found to be active in converting methanol to ethylene and propylene at a temperature between 250 and 350° C. The type and amount of the end product depend on the type of the catalyst and the MTO process used. Depending on the operating conditions, the weight ratio of propylene to ethylene can be modified between about 0.77 and 1.33, allowing considerable flexibility. For example, when using SAPO-34 according to an MTO process developed by UOP and Norsk Hydro, methanol is converted to ethylene and propylene at more than 80% selectivity, and also to butene, a valuable starting material for a number of products, at about 10%. While using an MTO process developed by Lurgi with ZSM-5 catalysts, mostly propylene is produced at yields above 70%. A process developed by ExxonMobil, with ZSM-5 catalyst, produces hydrocarbons in the gasoline and/or distillate range at selectivity greater than 95%.

There is also a methanol to gasoline (MTG) process, in which medium-pore zeolites with considerable acidity, e.g., ZSM-5, are used as catalysts. In this process, methanol is first dehydrated to an equilibrium mixture of dimethyl ether, methanol and water over a catalyst, and this mixture is then converted to light olefins, primarily ethylene and propylene. The light olefins can undergo further transformations to higher olefins, $C_3$-$C_6$ alkanes, and $C_6$-$C_{10}$ aromatics such as toluene, xylenes, and trimethylbenzene.

With decreasing oil and gas reserves, it is inevitable that synthetic hydrocarbons would play a major role. Thus, methanol-based synthetic hydrocarbons and chemicals available through MTG and MTO processes will assume increasing importance in replacing oil and gas-based materials. The listed uses of methanol is only illustrative and not limiting.

Methanol can also be used as a source of single cell proteins. A single cell protein (SCP) refers to a protein produced by a microorganism, which degrades hydrocarbon substrates while gaining energy. The protein content depends on the type of microorganism, e.g., bacteria, yeast, mold, etc. The SCP has many uses, including uses as food and animal feed.

Considering the numerous uses of methanol, it is clearly desirable to have improved and efficient methods of producing methanol. Currently, methanol is almost exclusively made from synthesis gas obtained from incomplete combustion (or catalytic reforming) of fossil fuel, mainly natural gas (methane) and coal.

Methanol can also be made from renewable biomass, but such methanol production also involves syn-gas and may not be energetically favorable and limited in terms of scale. As used herein, the term "biomass" includes any type of plant or animal material, i.e., materials produced by a life form, including wood and wood wastes, agricultural crops and their waste byproducts, municipal solid waste, animal waste, aquatic plants, and algae. The method of transforming biomass to methanol is similar to the method of producing methanol from coal, and requires gasification of biomass to syn-gas, followed by methanol synthesis by the same processes used with fossil fuel. Use of biomass also presents other disadvantages, such as low energy density and high cost of collecting and transporting bulky biomass. Although recent improvements involving the use of "biocrude," black liquid obtained from fast pyrolysis of biomass, is somewhat promising, more development is needed for commercial application of biocrude.

The presently existing method of producing methanol involves syn-gas. Syn-gas is a mixture of hydrogen, carbon monoxide and carbon dioxide, and produces methanol over a heterogeneous catalyst according to the following equations:

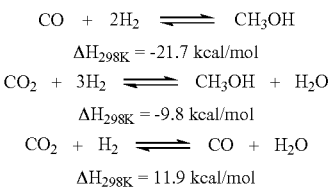

The first two reactions are exothermic with heat of reaction equal to $-21.7$ kcal.mol$^{-1}$ and $-9.8$ kcal.mol$^{-1}$, respectively, and result in a decrease in volume. Conversion to methanol is favored by increasing the pressure and decreasing the temperature according to Le Chatelier's principle. The third equation describes the endothermic reverse water gas shift reaction (RWGSR). Carbon monoxide produced in the third reaction can further react with hydrogen to produce methanol. The second reaction is simply the sum of the first and the third reactions. Each of these reactions is reversible, and is therefore limited by thermodynamic equilibrium under the reaction conditions, e.g., temperature, pressure and composition of the syn-gas.

Synthesis gas for methanol production can be obtained by reforming or partial oxidation of any carbonaceous material, such as coal, coke, natural gas, petroleum, heavy oil, and asphalt. The composition of syn-gas is generally characterized by the stoichiometric number S, corresponding to the equation shown below.

$$S = \frac{(\text{moles H}_2 - \text{moles CO}_2)}{(\text{moles CO} + \text{moles CO}_2)}$$

Ideally, S should be equal to or slightly above 2. A value above 2 indicates excess hydrogen, while a value below 2 indicates relative hydrogen deficiency. Reforming of feedstock having a higher H/C ratio, such as propane, butane or naphthas, leads to S values in the vicinity of 2, ideal for conversion to methanol. When coal or methane is used, however, additional treatment is required to obtain an optimal S value. Synthesis gas from coal requires treatment to avoid formation of undesired byproducts. Steam reforming of methane yields syn-gas with a stoichiometric number of 2.8 to 3.0, and requires lowering the S value closer to 2 by adding $CO_2$ or using excess hydrogen in some other process such as ammonia synthesis. However, natural gas is still the preferred feedstock for methanol production because it offers high hydrogen content and, additionally, the lowest energy consumption, capital investment and operating costs. Natural gas also contains fewer impurities such as sulfur, halogenated compounds, and metals which may poison the catalysts used in the process.

The existing processes invariably employ extremely active and selective copper-based catalysts, differing only in the reactor design and catalyst arrangement. Because only part of syn-gas is converted to methanol after passing over the catalyst, the remaining syn-gas is recycled after separation of methanol and water. There is also a more recently developed liquid phase process for methanol production, during which syn-gas is bubbled into liquid. Although the existing processes have methanol selectivity greater than 99% and energy efficiency above 70%, crude methanol leaving the reactor still contains water and other impurities, such as dissolved gas (e.g., methane, CO, and $CO_2$), dimethyl ether, methyl formate, acetone, higher alcohols (ethanol, propanol, butanol), and long-chain hydrocarbons. Commercially, methanol is available in three grades of purity: fuel grade, "A" grade, generally used as a solvent, and "AA" or chemical grade. Chemical grade has the highest purity with a methanol content exceeding 99.85% and is the standard generally observed in the industry for methanol production. The syn-gas generation and purification steps are critical in the existing processes, and the end result would largely depend on the nature and purity of the feedstock. To achieve the desired level of purity, methanol produced by the existing processes is usually purified by sufficient distillation. Another major disadvantage of the existing process for producing methanol through syn-gas is the energy requirement of the first highly endothermic steam reforming step. The process is also inefficient because it involves transformation of methane in an oxidative reaction to carbon monoxide (and some $CO_2$), which in turn must be reduced to methanol.

It is clearly desirable and maybe advantageous to produce methanol without first producing syn-gas. It would be further advantageous to use an abundant, practically unlimited resource such as carbon dioxide as the carbon source to produce methanol. For example, U.S. Pat. No. 5,928,806, the entire content of which is incorporated herein by reference thereto, discloses production of methanol, and related oxygenates and hydrocarbons, based on a carbon dioxide-based regenerative fuel cell concept.

When hydrocarbons are burned they produce carbon dioxide and water. It is clearly of great significance, if this process can be reversed and an efficient and economic process can be found to produce methanol from carbon dioxide and water to be subsequently used for energy storage, fuels and production of synthetic hydrocarbons. In plant photosynthesis, carbon dioxide is captured from the air and converted with water and solar energy into new plant life. Conversion of plant life into fossil fuel, however, is a very long process. Thus, it is highly desirable to develop a process for chemical recycling carbon dioxide to produce hydrocarbons in a short, commercially feasible time scale.

Carbon dioxide is known to be photochemically or electrochemically readily reduced to formic acid with formaldehyde and methanol being formed in only smaller amounts. Direct electrochemical reduction of $CO_2$ into methanol under pressure also provides methyl formate. Catalytic hydrogenation of carbon dioxide using heterogeneous catalysts provides methanol together with water as well as formic acid and formaldehyde. As the generation of needed hydrogen is highly energy consuming, the production of methanol with equimolar amount of water as well as other side products from carbon dioxide is not practical. No efficient ways for the selective high yield, high selectivity economical conversion of carbon dioxide to methanol is presently known. The high selectivity laboratory reduction of carbon dioxide to methanol with complex metal hydrides, such as lithium aluminum hydride is extremely costly and therefore not suited for the bulk production of methanol.

Attempts have been made to chemically convert $CO_2$ to methanol and subsequently to hydrocarbons by catalytic or electrochemical hydrogenation. Catalysts based on metals and their oxides, in particular copper and zinc, have been developed for this process. These catalysts are unexpectedly similar to the ones currently used for the conventional methanol production via syn-gas. It is now understood that methanol is most probably formed almost exclusively by hydrogenation of $CO_2$ contained in syn-gas on the surface of the catalyst. To be converted to methanol, CO present in the syn-gas first undergoes a water gas shift reaction to form $CO_2$ and $H_2$, and the $CO_2$ then reacts with hydrogen to produce methanol. One of the limiting factors for large scale use of such methanol conversion process is the availability of the feedstock, i.e., $CO_2$ and $H_2$. While $CO_2$ can be obtained relatively easily in large amounts from various industrial exhausts, hydrogen is mainly produced from non-renewable fossil fuel-based syn-gas and therefore has limited availability. Further, generation of hydrogen from fossil fuels has a high energy requirement.

Other methods for hydrogen production from fossil fuel have been investigated, including the "Carnol" process, in which thermal decomposition of methane produces hydrogen and solid carbon. The generated hydrogen is then reacted with $CO_2$ to produce methanol. This process is advantageous over methane steam reforming for requiring relatively less energy, about 9 kcal for producing one mole of hydrogen, and for producing a byproduct that can be more easily handled, stored and used, compared to $CO_2$ emissions generated by methane steam reforming or partial oxidation. However, the thermal decomposition of methane requires heating it to temperatures of above 800° C. and gives only relatively low yield of hydrogen. The process, in any case, requires substantial development for commercial application.

U.S. Publication No. 2006/0235091 describes that carbon dioxide can be used in the dry catalytic reforming of methane, if natural gas is available, producing carbon monoxide and hydrogen to be used to produce methanol.

A publication by Saeki et al. (Electrochemical Reduction of $CO_2$ with High Current Density In a $CO_2$-Methanol Medium. J. Phys. Chem. 1995, 99, 8440-8446) also reports that the electro chemical reduction of carbon dioxide in methanol solution under pressure was found to provide a high yield of methyl formate.

The methyl formate can be subsequently hydrogenatively converted exclusively to methanol. Formic acid can be used as the hydrogen source for the reduction of methyl formate to methanol over noble metal catalysts.

Otherwise, hydrogen used in catalytic hydrogenation can be obtained from any suitable source, such as electrolysis of water, using any suitable method and source of energy, e.g., atomic, solar, wind, geothermal, etc. Photolytic, thermal, enzymatic, and other means of cleavage of water to hydrogen is also possible.

In the above-described processes, a hydrogen source must be added to the reaction mixture for conversion to methanol. If methanol could be produced on a large scale directly from electrochemical reduction of carbon dioxide, without the extra step of adding a hydrogen source, such a process would be advantageous considering the abundant supply of carbon dioxide in the atmosphere and in industrial exhausts of fossil fuel power burning power plants and cement plants. It would at the same time also mitigate greenhouse effect that is causing the global climate change (i.e., global warming). The present invention now provides such a process to obtain these benefits.

SUMMARY OF THE INVENTION

The invention relates to various embodiments of an environmentally beneficial method for producing methanol by reductive conversion of an available source of carbon dioxide including flue gases of fossil fuel burning power plants, industrial exhaust gases or the atmosphere itself. The method includes electrochemically reducing the carbon dioxide in a divided electrochemical cell that includes an anode in one cell compartment and a metal cathode electrode in another cell compartment that also contains an aqueous solution or aqueous methanolic solution and an electrolyte of one or more alkyl ammonium halides, alkali carbonates or combinations thereof to produce therein a reaction mixture containing carbon monoxide and hydrogen which can be subsequently used to produce methanol while also producing oxygen in the cell at the anode.

The alkyl ammonium halides include multi-alkyl ammonium halides and preferably tetrabutylammonium halides. In another embodiment, the tetrabutylammonium halide is selected from the group consisting of tetrabutylammonium bromide, tetrabutylammonium chloride, tetrabutylammonium iodide or mixtures thereof. The alkali carbonates include bicarbonates such as sodium or potassium bicarbonates and the like.

While the electrode may be chosen from any suitable metal electrode, such as Cu, Au, Ag, Zn, Pd, Ga, Ni, Hg, In, Sn, Cd, Ti, Pb, and Pt, preferably the metal electrode is a gold electrode. The metal electrode acts as a catalyst for the electrochemical reduction.

In the embodiment, the electrochemical reduction includes applying a voltage of about −1.5 to −4 V with respect to a Ag/AgCl electrode to produce the reaction.

Advantageously, the carbon dioxide used in the reaction is obtained from an exhaust stream from fossil fuel burning power or industrial plants, from geothermal or natural gas wells. The available carbon dioxide, however, may also be obtained from the atmosphere by absorbing atmospheric carbon dioxide onto a suitable adsorbent followed by treating the adsorbent to release the adsorbed carbon dioxide therefrom. In this embodiment, the adsorbent is treated by sufficient heating to release the adsorbed carbon dioxide, or may also be treated by subjecting the adsorbent to sufficient reduced pressure to release the adsorbed carbon dioxide.

The electrical energy for the electrochemical reducing of carbon dioxide can come from a conventional energy source, including nuclear and alternatives (hydroelectric, wind, solar power, geothermal, etc.).

BRIEF DESCRIPTION OF THE DRAWINGS

The benefits of the invention will become more evident from a review of the following detailed description of illustrative embodiments and the accompanying drawings, wherein.

DETAILED DESCRIPTION OF THE PREFERRED EMBODIMENTS

Figure 1:
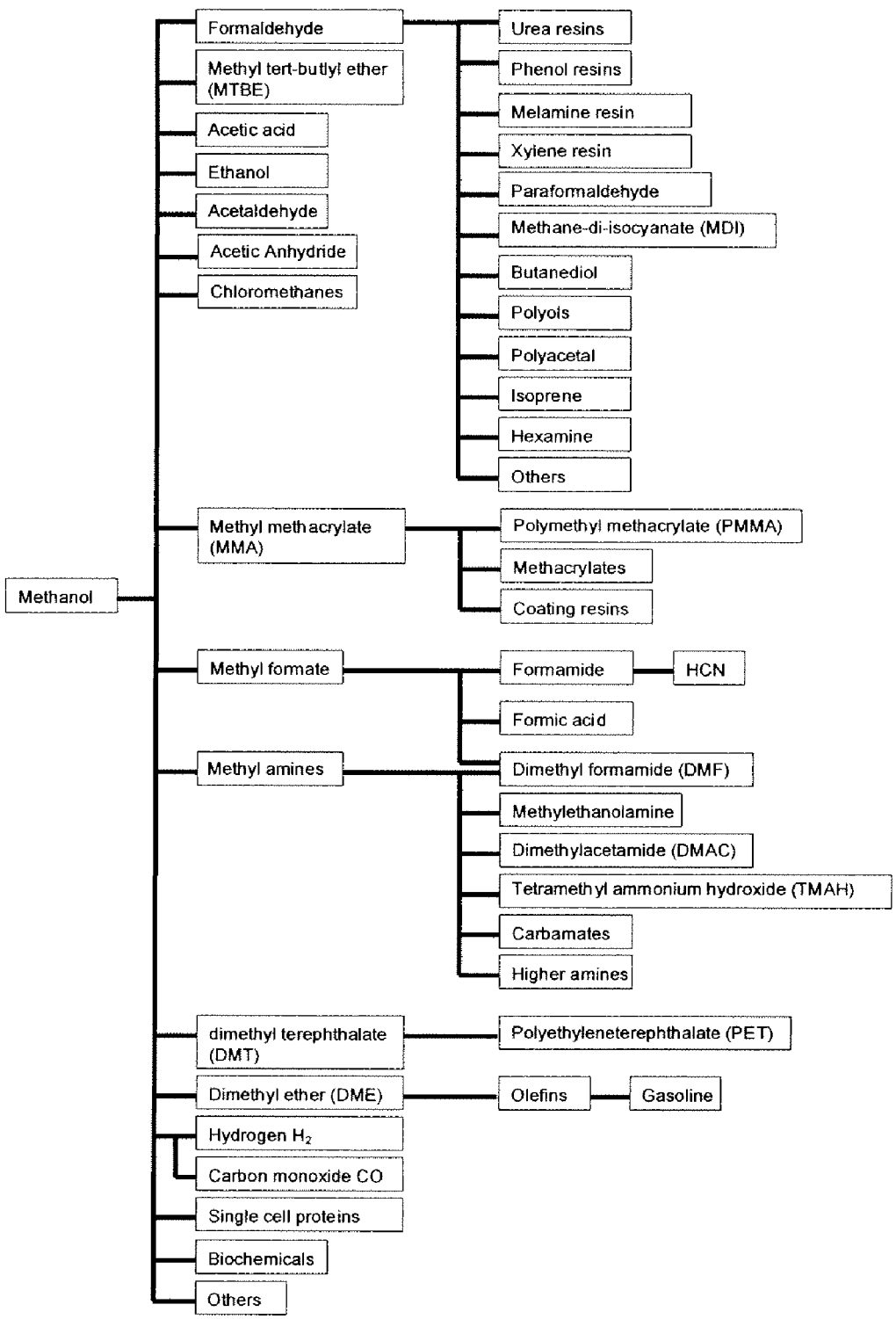
FIG. 1 shows known examples of methanol-derived chemical products and materials.

The present invention relates to the simple, efficient, and economical conversion of carbon dioxide from flue gases of fossil fuel burning power plants, industrial exhaust gases, carbon dioxide accompanying natural gas, carbon dioxide accompanying steam from geothermal wells or from the atmosphere itself to methanol, with subsequent application for energy storage and transportation fuels, conversion to synthetic hydrocarbons and its products. The carbon dioxide to methanol conversion is a better alternative to sequestration making it a renewable general carbon source for fuels, synthetic hydrocarbons and their products. The use of this process of converting carbon dioxide to methanol and its products will also lead to a significant reduction of carbon dioxide, a major greenhouse gas, in the atmosphere thus mitigating global warming.

Carbon dioxide is preferably obtained from concentrated point sources of its generation prior to its release into the atmosphere. Carbon dioxide can, however, also be obtained by separating atmospheric carbon dioxide with a suitable adsorbent followed by desorption treatment to release the adsorbed carbon dioxide therefrom, as disclosed in PCT Application No. WO 2008/021700. This can be achieved by heating to release the adsorbed carbon dioxide, by treating it under reduced pressure or by a suitable combination of both.

Methanol produced according to the discussed processes can be used for any purpose, such as for energy storage and transportation, as a fuel in internal combustion engines or fuel cells, to produce related fuels (dimethyl ether, by dehydration), dimethyl carbonate (by oxidative carbonylation), to produce ethylene, propylene, higher olefins, synthetic hydrocarbons and all their derived products including and not limited to single cell proteins.

High concentration carbon dioxide sources are those frequently accompanying natural gas in amounts of 5 to 50%, those from flue gases of fossil fuel (coal, natural gas, oil, etc.) burning power plants, exhaust of cement plants and other industrial sources. Certain geothermal steam also contains significant amounts of $CO_2$.

It has now been discovered that the use of electrochemical reduction of carbon dioxide ($CO_2$), tailored over certain cathode electrocatalysts produces carbon monoxide (CO) and hydrogen gas ($H_2$) in a high yielding ratio of approximately 1:2. The ratio can be between 1:2 and 1:2.1 with 1:2.05 being optimal regarding efficiency and reactant cost. Electrochemical reduction of $CO_2$ on metal electrodes such as Cu, Au, Ag, Zn, Pd, Ga, Ni, Hg, In, Sn, Cd, Tl, Pb, and Pt can give either methyl formate or CO using a variety of electrolytes and solvents (Y. Hori, H. Wakabe, T. Tsuamoto and O. Koga, *Electrochimica Acta*, 1994, 39, 1833-1839). The gold (Au) electrode has been found particularly effective for the production of CO.

It has further been discovered that the electrochemical reduction of $CO_2$ using noble metal, preferentially a gold electrode as a catalyst in aqueous methanol (or in water) with tetrabutylammonium halides and alkali carbonates as electrolytes not only gives CO but also $H_2$ at the cathode, while producing oxygen gas ($O_2$) at the anode. Suitable tetrabutylammonium halides for use in the present invention include tetrabutylammonium bromide, tetrabutylammonium chloride and tetrabutylammonium iodide. Tetraalkyl ammonium slats are known to promote one electron reduction of $CO_2$.

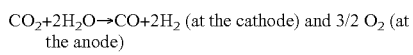
$CO_2 + 2H_2O \rightarrow CO + 2H_2$ (at the cathode) and $3/2\ O_2$ (at the anode)

The CO and $H_2$ produced at the cathode are subsequently reacted over Cu and Ni based catalysts to produce high yields of methanol ($CH_3OH$).

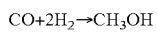
$CO + 2H_2 \rightarrow CH_3OH$

The specific conditions for the above-described chemical reactions are generally known to skilled chemists and optimum conditions can be readily established for the reactions. Typical yields are about 60 to 100%, based on the amount of $CO_2$, preferably about 75 to 90%, and more preferably about 85 to 95%. At a proper voltage, i.e. about −1.5 to −4 V with respect to an $Ag^0/AgCl$ electrode, a ratio of about 1:2 of CO and $H_2$ can be produced with good columbic efficiency at the cathode.

The electrochemical reduction of $CO_2$ can also be achieved efficiently using $KHCO_3$ as the electrolyte in aqueous medium. $CO_2$ is readily reduced in the aqueous medium over gold electrode to an optimal 1:2 (CO to $H_2$) ratio at the cathode at −3.2V. The columbic efficiences are quite high reaching 100%. Pure oxygen is produced at the anode. The electricity needed for the electrochemical reduction can come from any source including nuclear or alternative energy (hydro, wind, solar, geothermal, etc.).

The present invention advantageously produces methanol without the need of adding extra reactants, such as a hydrogen source. There is also no need to separate the product mixture in a subsequent treatment step, thereby streamlining methanol production.

The use of carbon dioxide based methanol is highly desirable as it can mitigate and eventually replace the world's reliance on fossil fuels. In addition, the reduction in carbon dioxide emissions as well as the removal of excess carbon dioxide from the atmosphere will assist in reducing global warming and restoring atmospheric conditions to a pre-industrial level, thus preserving the planet's climate for future generations.

$CO_2$ emissions from fossil fuel burning power plants and varied industries including geothermal wells can be captured on-site. Separation of $CO_2$ from such exhausts is well-developed. The capture and use of existing atmospheric $CO_2$ allows chemical recycling of $CO_2$ as a renewable and unlimited source of carbon. $CO_2$ absorption facilities can be placed proximate to a hydrogen production site to enable subsequent methanol synthesis. When the processes of the invention utilize carbon dioxide from the atmosphere, the carbon dioxide can be separated and absorbed by using various processes as described in published PCT Application No. WO 2008/021700 and U.S. Pat. No. 7,378,561 or can be recycled chemically as described in published US Patent Application Nos. 2006/0235091 and 2007/0254969. Although the $CO_2$ content in the atmosphere is low (only 0.037%), the atmosphere offers an abundant and unlimited supply because $CO_2$ is recycled. For using atmospheric carbon dioxide efficiently, $CO_2$ absorption facilities are needed. This can be addressed by using efficient $CO_2$ absorbents such as polyethyleneimines, polyvinylpyridines, polyvinylpyrroles, etc., on suitable solid carriers (e.g., active carbon, polymer, silica or alumina), which allow absorbtion of even the low concentration of atmospheric $CO_2$. $CO_2$ can also be captured using basic absorbents such as calcium hydroxide ($Ca(OH)_2$) and potassium hydroxide (KOH), which react with $CO_2$ to form calcium carbonate ($CaCO_3$) and potassium carbonate ($K_2CO_3$), respectively. $CO_2$ absorption is an exothermic reaction, which liberates heat, and is readily achieved by contacting $CO_2$ with an appropriate base. After capture, $CO_2$ is recovered from the absorbent by desorption, through heating, vacuum (or reduced pressure) or electrochemical treatment. Calcium carbonate, for example, is thermally calcinated to release carbon dioxide. As desorption is an endothermic, energy-demanding step, the appropriate treatment can be chosen to optimize absorption and desorption with the lowest possible energy input. Thus, $CO_2$ can be recycled by operation of absorbing-desorbing columns in convenient cycles with modest heating and/or under reduced pressure to cause desorption of $CO_2$ to take place.

When methanol, methanol-derived fuels or synthetic hydrocarbons are combusted (oxidatively used), they release $CO_2$ and water, thus providing the basis methanol cycle, the artificial version of the natural recycling of $CO_2$ through photosynthesis. In contrast to the nonrenewable fossil fuel sources such as oil, gas, and coal, recycling carbon dioxide from industrial and natural sources to produce methanol not only addresses the problem of diminishing fossil fuel resources, but also helps alleviate global warming due to greenhouse effect.

The effective electrochemical hydrogenative recycling of carbon dioxide disclosed herein provides new methods of producing methanol in an improved, efficient, and environmentally beneficial way, while mitigating $CO_2$ caused climate change (global warming). The use of methanol as a energy storage and transportation material eliminates many difficulties of using hydrogen for such purposes. The safety and versatility of methanol makes the disclosed recycling of carbon dioxide further desirable.

As known in the art, methanol can be easily treated to produce varied derived compounds including dimethyl ether, produced by dehydration of methanol, and dimethyl carbonate, produced by reaction of the methanol by oxidative carbonylation. Methanol and methanol-derived compounds, e.g., DME and DMC as oxygenated additives, can be blended with gasoline and used in internal combustion engines with only minor modifications. For example, methanol can be added to gasoline up to 85% by volume to prepare M85 fuel. Methanol can also be used to generate electricity in fuel cells, by either first catalytically reforming methanol to $H_2$ and CO or by reacting methanol directly with air in a direct methanol fuel cell (DMFC). DMFC greatly simplifies the fuel cell technology and makes it readily available to a wide range of applications, including portable mobile electronic devices and electricity generators.

In addition to being a conveniently storable energy source and fuel, methanol and methanol-derived DME and DMC are useful starting materials for various chemicals such as formaldehyde, acetic acid, and a number of other products including polymers, paints, adhesives, construction materials, synthetic chemicals, pharmaceuticals, and single cell proteins.

Methanol and/or dimethyl ether can also be conveniently converted in a single catalytic step to ethylene and/or propylene (e.g., in a methanol to olefin or "MTO" process), the building blocks for producing synthetic hydrocarbons and their products. This means that the hydrocarbon fuels and products currently derived from oil and natural gas can be obtained from methanol, which itself can advantageously be obtained from simple chemical recycling of atmospheric or industrial $CO_2$ sources. Another utilization of methanol is its ready conversion to ethanol via hydration of derived ethylene. Many further applications are known and can be applied to carbon dioxide derived methanol. It should be emphasized that there is no preference for any particular energy source needed for producing methanol. All sources, including alternative sources and atomic energy can be used. Energy once produced must be, however, stored and transported, for which methanol is well suited.

The improved and efficient selective conversion of carbon dioxide, which can be from atmospheric or industrial exhaust sources, to methanol according to the present invention also provides the needed raw material for what the inventors have termed the METHANOL ECONOMY™ process. This allows convenient storage and transport of energy in a liquid product that can be used as a fuel in internal combustion engines or in fuel cells and as a starting material for synthetic hydrocarbons and their varied products. The METHANOL ECONOMY™ process is based on the efficient direct conversion of still available natural gas resources to methanol or dimethyl ether, as disclosed in U.S. Publications Nos. 2006/0235088 and 2006/0235091, and 2007/0254969 as well as the presently disclosed reductive chemical conversion of carbon dioxide. The concept of the METHANOL ECONOMY™ process presents significant advantages and possibilities. In the METHANOL ECONOMY™ process, methanol is used as (1) convenient energy storage medium, which allows convenient and safe storage and handling; (2) readily transported and dispensed fuel, including for methanol fuel cells; and (3) feedstock for synthetic hydrocarbons and their products currently obtained from oil and gas resources, including polymers and even single cell proteins, which can be used for animal feed or human consumption. The environmental benefits obtained by disclosed chemical recycling of carbon dioxide results in mitigating the global warming to ensure the well being of future generations.

As methanol is readily dehydrated to dimethyl ether, the disclosed conversion of carbon dioxide to methanol is also adaptable to produce dimethyl ether for fuel and chemical applications as previously noted.

The disclosed new efficient production of methanol from industrial or natural carbon dioxide sources, or even from the air itself, provides the needed raw material for replacing the diminishing fossil fuel through the METHANOL ECONOMY™ process. The conversion of carbon dioxide to methanol necessitates significant energy, which can be, however, provided by any energy source including offpeak electric power of fossil fuel (e.g., coal) burning power plants, atomic energy or any alternative energy sources (solar, wind, geothermal, hydro, etc.). The reduction of $CO_2$ to methanol allows storage and transportation of energy in a convenient liquid product (i.e., methanol) more convenient, economical and safe than volatile hydrogen gas. Methanol and/or dimethyl ether are efficient fuels in internal combustion engines or in direct oxidation methanol fuel cells (DMFC as well as raw materials for olefins, synthetic hydrocarbons and varied products). The present invention greatly extends the scope of the utilization of carbon dioxide for the production of methanol and/or dimethyl ether from natural or industrial sources, even from the air itself.

EXAMPLES

The following examples illustrate the most preferred embodiments of the invention without limiting it.

Example 1

In a divided electrochemical cell, using tetrabutylammonium halides, preferentially tetrabutylammonium bromide as the electrolyte over gold electrode (cathode) in aqueous methanol medium at either −1.5V or −4V vs. Ag/AgCl reference electrode, $CO_2$ is reduced and water is electrolyzed to an optimal 1:2 mixture of CO and $H_2$ at the cathode. Pure oxygen as well as some bromine is produced at the anode.

Example 2

In a divided electrochemical cell, using, aqueous 0.1M $KHCO_3$ as the electrolyte $CO_2$ is reduced at the gold cathode at −3.2V vs. Ag/AgCl reference electrode $CO_2$ is reduced and water is electrolyzed to an optimal 1:2 mixture of CO and $H_2$ suitable for methanol synthesis. The total faradaic efficiencies for CO and $H_2$ production add up to 100%. Pure oxygen is produced at the anode.

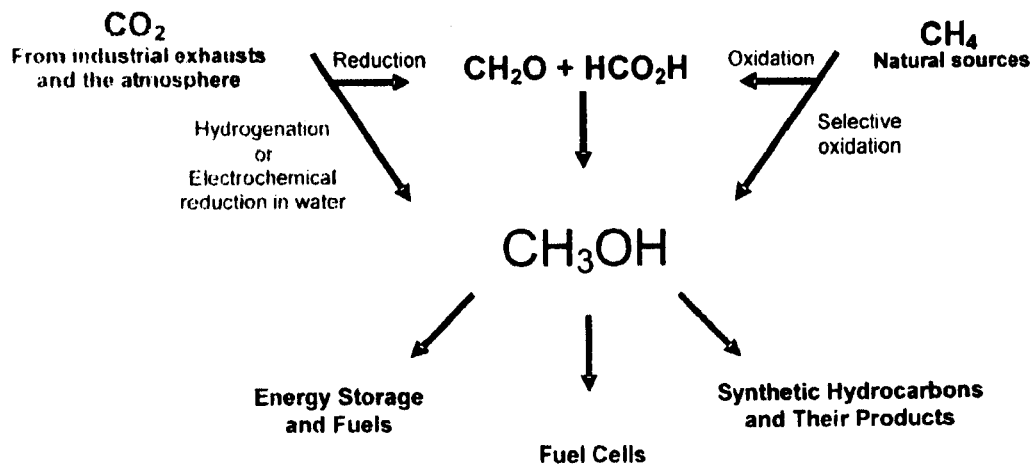

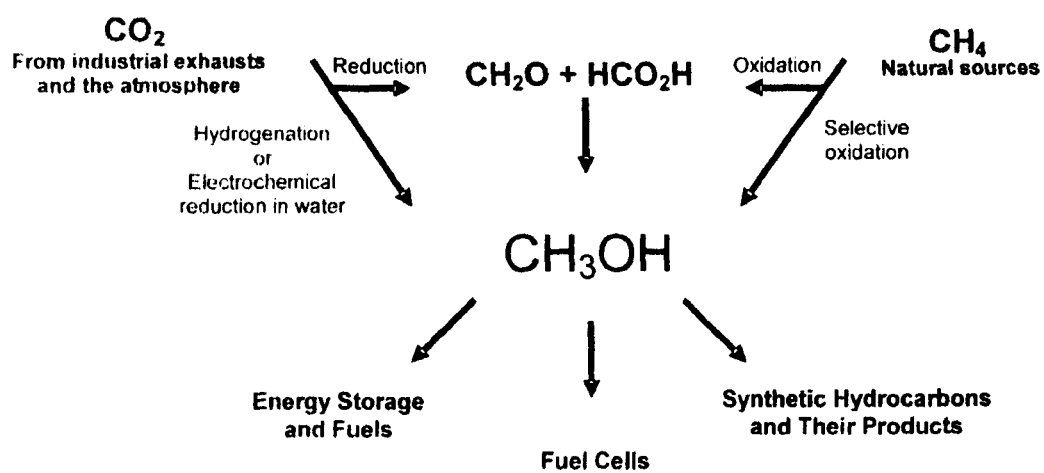

What is claimed is:

1. An environmentally beneficial method of producing methanol by recycling and reductive conversion of any available source of carbon dioxide, which comprises:
    providing a divided electrochemical cell comprising an anode in a first cell compartment and a metal cathode electrode in a second cell compartment that also contains an aqueous solution or aqueous methanolic solution of an electrolyte of one or more alkyl ammonium halides, alkali carbonates or combinations thereof;
    recycling carbon dioxide from an existing source into the second cell compartment;
    electrochemically reducing the recycled carbon dioxide and solution in the second cell compartment to produce therein a reaction mixture containing carbon monoxide and hydrogen gas; and
    obtaining the carbon monoxide and hydrogen gas of the reaction mixture from the second cell compartment and directly reacting the reaction mixture in the presence of a catalyst to produce methanol while also producing oxygen in the first cell compartment at the anode to benefit the environment by reducing atmospheric carbon dioxide.

2. The method of claim 1 wherein the carbon monoxide and hydrogen gas are obtained in the reaction mixture in a ratio of at least about 1:2 or with excess amounts of hydrogen gas, and without adding hydrogen from outside of the cell.

3. The method of claim 1, wherein the carbon monoxide and hydrogen gas are present in the reaction mixture in a ratio of 1:2 to 1:2.1.

4. The method of claim 1, wherein the electrolyte comprises
    (1) one or more multi-alkyl ammonium halides, one or more alkali carbonates or bicarbonates; and
    (2) methanol or water.

5. The method of claim 4, wherein the multi-alkyl ammonium halides are tetrabutylammonium halides.

6. The method of claim 5, wherein the tetrabutylammonium halides are selected from the group consisting of tetrabutylammonium bromide, tetrabutylammonium chloride, tetrabutylammonium iodide and mixtures thereof.

7. The method of claim 1, wherein the alkali carbonates are sodium or potassium bicarbonates.

8. The method of claim 1, wherein the metal cathode electrode is a Cu, Au, Ag, Zn, Pd, Ga, Ni, Hg, In, Sn, Cd, Tl, Pb or Pt electrode.

9. The method of claim 8, wherein the metal cathode electrode is a gold electrode.

10. The method of claim 1, wherein the electrochemical reduction includes applying a voltage of from −1.5 to −4 V with respect to a Ag/AgCl reference electrode.

11. The method of claim 1, wherein the existing source is an exhaust stream from a fossil fuel burning power or industrial plant, from a source accompanying natural gas or from geothermal wells and wherein the carbon dioxide is obtained from such existing source.

12. The method of claim 1, wherein the existing source is the atmosphere and which further comprises obtaining the carbon dioxide from such existing source by absorbing atmospheric carbon dioxide onto a suitable adsorbent followed by treating the adsorbent to release the adsorbed carbon dioxide therefrom.

13. The method of claim 12, wherein the adsorbent is treated by sufficient heating or by subjecting the adsorbent to sufficient reduced pressure to release the adsorbed carbon dioxide.

14. The method of claim 1, wherein electrical energy for the electrochemical reduction of the carbon dioxide is provided from an energy source based on nuclear, hydroelectric, wind, geothermal or solar power.

15. An environmentally beneficial method of producing methanol by recycling and reductive conversion of any available source of carbon dioxide, which comprises:
    providing a divided electrochemical cell comprising an anode in a first cell compartment and a noble metal cathode electrode in a second cell compartment, with the second cell compartment also containing an aqueous solution or aqueous methanolic solution of an electrolyte of one or more tetrabutylammonium halides or alkali carbonates;
    recycling carbon dioxide from an existing source into the second cell compartment;
    electrochemically reducing the recycled carbon dioxide and solution in the second cell compartment by applying a voltage to produce therein a reaction mixture containing carbon monoxide and hydrogen gas with the reaction mixture containing excess amounts of hydrogen gas without adding hydrogen from outside of the electrochemical cell while also producing oxygen at the anode in the first cell compartment; and obtaining the carbon monoxide and hydrogen gas of the reaction mixture from the second cell compartment and directly reacting the reaction mixture in the presence of a catalyst to produce methanol while producing the oxygen in the first cell compartment at the anode to benefit the environment by reducing atmospheric carbon dioxide.

16. The method of claim 15 wherein the existing source is an exhaust stream from a fossil fuel burning power or industrial plant, from a source accompanying natural gas, from a geothermal well or from the atmosphere, wherein the carbon dioxide is obtained from such existing source; and providing electrical energy for the electrochemical reduction from an energy source based on nuclear, hydroelectric, wind, geothermal or solar power thus providing environmental benefits.

17. The method of claim 16, wherein the carbon monoxide and hydrogen gas are present in the reaction mixture in a ratio of 1:2 to 1:2.1, the metal cathode electrode is a gold electrode, and a voltage is applied in a range from −1.5 to −4 V with respect to a Ag/AgCl reference electrode.

* * * * *

UNITED STATES PATENT AND TRADEMARK OFFICE
CERTIFICATE OF CORRECTION

PATENT NO. : 7,704,369 B2
APPLICATION NO. : 12/171904
DATED : April 27, 2010
INVENTOR(S) : Olah et al.

It is certified that error appears in the above-identified patent and that said Letters Patent is hereby corrected as shown below:

Title Page:
Delete title page showing an illustrative figure and substitute the attached title page therefor.
Item (56) References Cited, OTHER PUBLICATIONS: Saeki et al. reference (second occurrence), before "Electrochemical" delete "("; and before "with High Current" change "CQ" to -- $CO_2$ --.

Figure 2:
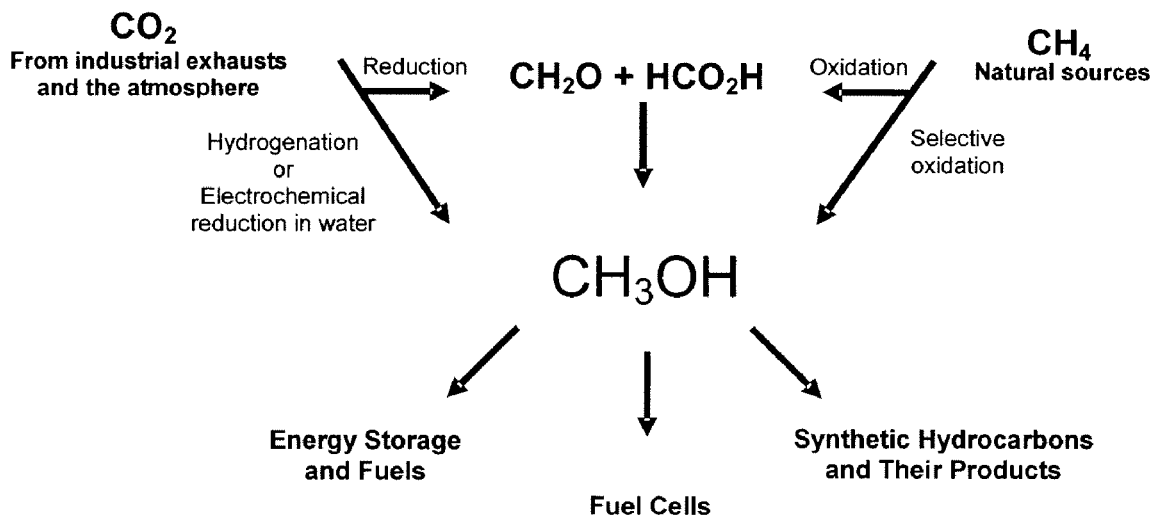
FIG. 2 schematically illustrates the METHANOL ECONOMY™ process.

Drawings:
FIG. 2, in the heading "The Methanol Economy®", delete the "®" symbol.
Delete drawing figure 2, and substitute the attached figure 2 therefor.

Column 11:
Line 33, after "ECONOMY", delete the "™" symbol.

Column 14:
Line 39, after "ECONOMY", delete the "™" symbol.
Line 44, after "ECONOMY", delete the "™" symbol.
Line 50, after "ECONOMY", delete the "™" symbol.
Line 51, after "ECONOMY", delete the "™" symbol.

Column 15:
Line 3, after "ECONOMY", delete the "™" symbol.

Signed and Sealed this

Thirty-first Day of August, 2010

David J. Kappos
*Director of the United States Patent and Trademark Office*

United States Patent
Olah et al.

(10) Patent No.: US 7,704,369 B2
(45) Date of Patent: Apr. 27, 2010

(54) ELECTROLYSIS OF CARBON DIOXIDE IN AQUEOUS MEDIA TO CARBON MONOXIDE AND HYDROGEN FOR PRODUCTION OF METHANOL

(75) Inventors: George A. Olah, Beverly Hills, CA (US); G. K. Surya Prakash, Hacienda Heights, CA (US)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 12/171,904

(22) Filed: Jul. 11, 2008

(65) Prior Publication Data
US 2009/0014336 A1    Jan. 15, 2009

Related U.S. Application Data

(60) Provisional application No. 60/949,723, filed on Jul. 13, 2007.

(51) Int. Cl.
    C25B 3/00       (2006.01)
    C07C 27/00      (2006.01)
(52) U.S. Cl. .................................. 205/450; 568/700
(58) Field of Classification Search ............ 205/450, 205/555, 628, 638; 568/700
    See application file for complete search history.

(56) References Cited

U.S. PATENT DOCUMENTS 4,022,672 A  *  5/1977  Alvarez et al. ............ 205/461
6,797,830 B2 *  9/2004  Tanaka et al. ............. 549/273
2006/0048517 A1 *  3/2006  Fradette et al. ............ 60/772
2007/0045125 A1    3/2007  Hartvigsen et al. ....... 205/637
2007/0129450 A1 *  6/2007  Barnicki et al. .......... 518/704

FOREIGN PATENT DOCUMENTS

JP       08246177 A   *  9/1996
RU       2 062 750 C1    6/1996
WO       WO 02083272 A1 * 10/2002

OTHER PUBLICATIONS

Kobayashi et al., "Novel CO2 Electrochemical Reduction to Methanol for H2 Storage", Energy & Fuels (no month, 2004), vol. 18, pp. 285-286.*
Sanchez et al., "Electrochemical Approaches to Alleviation of the Problem of Carbon Dioxide Accumulation", Pure Appl. Chem. (no month, 2001), vol. 73, No. 12, pp. 1917-1927.*
Ogden et al., "Electrolytic Hydrogen From Thin-Film Solar Cells", Int. J. Hydrogen Energy (no month, 1990), vol. 15, No. 3, pp. 155-169.*

(Continued)

Primary Examiner—Edna Wong
(74) Attorney, Agent, or Firm—Winston & Strawn LLP

(57) ABSTRACT

An environmentally beneficial method of producing methanol from varied sources of carbon dioxide including flue gases of fossil fuel burning power plants, industrial exhaust gases or the atmosphere itself. Converting carbon dioxide by an electrochemical reduction of carbon dioxide in a divided electrochemical cell that includes an anode in one cell compartment and a metal cathode electrode in another cell compartment that also contains an aqueous solution comprising methanol and an electrolyte of one or more alkyl ammonium halides, alkali carbonates or combinations thereof to produce therein a reaction mixture containing carbon monoxide and hydrogen which can be subsequently used to produce methanol while also producing oxygen in the cell at the anode.

17 Claims, 2 Drawing Sheets